United States Patent
Frushour

(10) Patent No.: US 10,172,612 B2
(45) Date of Patent: Jan. 8, 2019

(54) SURGICAL INSTRUMENTS WITH FORCE APPLIER AND METHODS OF USE

(71) Applicant: COVIDIEN LP, Mansfield, MA (US)

(72) Inventor: Scott E. M. Frushour, Boulder, CO (US)

(73) Assignee: COVIDIEN LP, Mansfield, MA (US)

( * ) Notice: Subject to any disclaimer, the term of this patent is extended or adjusted under 35 U.S.C. 154(b) by 521 days.

(21) Appl. No.: 14/883,088

(22) Filed: Oct. 14, 2015

(65) Prior Publication Data

US 2016/0206336 A1     Jul. 21, 2016

Related U.S. Application Data

(60) Provisional application No. 62/105,961, filed on Jan. 21, 2015.

(51) Int. Cl.
    *A61B 18/12*     (2006.01)
    *A61B 17/068*     (2006.01)
    (Continued)

(52) U.S. Cl.
    CPC .......... *A61B 17/068* (2013.01); *A61B 5/1072* (2013.01); *A61B 17/07207* (2013.01);
    (Continued)

(58) Field of Classification Search
    CPC ............ A61B 17/068; A61B 17/07207; A61B 18/1445; A61B 2017/00022;
    (Continued)

(56) References Cited

U.S. PATENT DOCUMENTS 1,731,069 A     10/1929     Herman
D249,549 S     9/1978     Pike
(Continued)

FOREIGN PATENT DOCUMENTS

CN     201299462     9/2009
DE     2415263 A1     10/1975
(Continued)

OTHER PUBLICATIONS

Michael Choti, "Abdominoperineal Resection with the LigaSure Vessel Sealing System and LigaSure Atlas 20 cm Open Instrument"; Innovations That Work, Jun. 2003.
(Continued)

*Primary Examiner* — Daniel Fowler

(57) ABSTRACT

A surgical instrument including a housing, an elongated portion, an end effector, a drive beam and a force applier is provided. The housing includes a first actuator and a second actuator. The elongated portion extends distally from the housing and defines a longitudinal axis. The end effector is disposed adjacent a distal portion of the elongated portion, and includes a first jaw member and a second jaw member. The first jaw member has a cavity defined therein. Actuation of the first actuator causes distal translation of the drive beam to move the first jaw member relative to the second jaw member toward the approximated position, which applies a fist force against tissue disposed between the jaw members. Actuation of the second actuator causes distal translation of the force applier such that at least a portion of the force applier moves into the cavity of the first jaw member and applies an additional force against tissue disposed between the jaw members.

6 Claims, 5 Drawing Sheets

(51) Int. Cl.
*A61B 18/14* (2006.01)
*A61B 17/072* (2006.01)
*A61B 34/35* (2016.01)
*A61B 5/107* (2006.01)
*A61B 18/00* (2006.01)
*A61B 17/29* (2006.01)
*A61B 17/00* (2006.01)

(52) U.S. Cl.
CPC .......... *A61B 18/1445* (2013.01); *A61B 34/35* (2016.02); *A61B 2017/00022* (2013.01); *A61B 2017/07257* (2013.01); *A61B 2017/2902* (2013.01); *A61B 2017/2932* (2013.01); *A61B 2017/2933* (2013.01); *A61B 2017/2938* (2013.01); *A61B 2018/0063* (2013.01); *A61B 2018/00303* (2013.01); *A61B 2018/00601* (2013.01); *A61B 2018/00642* (2013.01); *A61B 2018/00791* (2013.01); *A61B 2018/00875* (2013.01); *A61B 2018/1455* (2013.01); *A61B 2562/0257* (2013.01)

(58) Field of Classification Search
CPC .. A61B 2017/07257; A61B 2017/2902; A61B 2017/2932; A61B 2017/2933; A61B 2017/2938; A61B 2018/00303; A61B 2018/00601; A61B 2018/0063; A61B 2018/00642; A61B 2018/00791; A61B 2018/00875; A61B 2018/1455
See application file for complete search history.

(56) References Cited

U.S. PATENT DOCUMENTS

| | | | |
|---|---|---|---|
| D263,020 S | | 2/1982 | Rau, III |
| D295,893 S | | 5/1988 | Sharkany et al. |
| D295,894 S | | 5/1988 | Sharkany et al. |
| D298,353 S | | 11/1988 | Manno |
| D299,413 S | | 1/1989 | DeCarolis |
| 5,147,357 A | * | 9/1992 | Rose .............. A61B 17/29 606/49 |
| D343,453 S | | 1/1994 | Noda |
| D348,930 S | | 7/1994 | Olson |
| D349,341 S | | 8/1994 | Lichtman et al. |
| D354,564 S | | 1/1995 | Medema |
| D358,887 S | | 5/1995 | Feinberg |
| 5,626,607 A | | 5/1997 | Malecki et al. |
| D384,413 S | | 9/1997 | Zlock et al. |
| 5,673,841 A | | 10/1997 | Schulze et al. |
| 5,762,609 A | | 6/1998 | Benaron et al. |
| H1745 H | | 8/1998 | Paraschac |
| D402,028 S | | 12/1998 | Grimm et al. |
| 5,876,401 A | | 3/1999 | Schulze et al. |
| D408,018 S | | 4/1999 | McNaughton |
| D416,089 S | | 11/1999 | Barton et al. |
| D424,694 S | | 5/2000 | Tetzlaff et al. |
| D425,201 S | | 5/2000 | Tetzlaff et al. |
| H1904 H | | 10/2000 | Yates et al. |
| D449,886 S | | 10/2001 | Tetzlaff et al. |
| D453,923 S | | 2/2002 | Olson |
| D454,951 S | | 3/2002 | Bon |
| D457,958 S | | 5/2002 | Dycus et al. |
| D457,959 S | | 5/2002 | Tetzlaff et al. |
| H2037 H | | 7/2002 | Yates et al. |
| 6,454,762 B1 | | 9/2002 | Rosler et al. |
| D465,281 S | | 11/2002 | Lang |
| D466,209 S | | 11/2002 | Bon |
| D493,888 S | | 8/2004 | Reschke |
| D496,997 S | | 10/2004 | Dycus et al. |
| D499,181 S | | 11/2004 | Dycus et al. |
| D502,994 S | | 3/2005 | Blake, III |
| D509,297 S | | 9/2005 | Wells |
| D525,361 S | | 7/2006 | Hushka |
| D531,311 S | | 10/2006 | Guerra et al. |
| D533,274 S | | 12/2006 | Visconti et al. |
| D533,942 S | | 12/2006 | Kerr et al. |
| D535,027 S | | 1/2007 | James et al. |
| D538,932 S | | 3/2007 | Malik |
| D541,418 S | | 4/2007 | Schechter et al. |
| D541,611 S | | 5/2007 | Aglassinger |
| D541,938 S | | 5/2007 | Kerr et al. |
| D545,432 S | | 6/2007 | Watanabe |
| D547,154 S | | 7/2007 | Lee |
| D564,662 S | | 3/2008 | Moses et al. |
| D567,943 S | | 4/2008 | Moses et al. |
| D575,395 S | | 8/2008 | Hushka |
| D575,401 S | | 8/2008 | Hixson et al. |
| D582,038 S | | 12/2008 | Swoyer et al. |
| 7,491,202 B2 | | 2/2009 | Odom et al. |
| D617,900 S | | 6/2010 | Kingsley et al. |
| D617,901 S | | 6/2010 | Unger et al. |
| D617,902 S | | 6/2010 | Twomey et al. |
| D617,903 S | | 6/2010 | Unger et al. |
| D618,798 S | | 6/2010 | Olson et al. |
| 7,731,717 B2 | | 6/2010 | Odom et al. |
| D621,503 S | | 8/2010 | Otten et al. |
| 7,776,037 B2 | | 8/2010 | Odom |
| D627,462 S | | 11/2010 | Kingsley |
| D628,289 S | | 11/2010 | Romero |
| D628,290 S | | 11/2010 | Romero |
| D630,324 S | | 1/2011 | Reschke |
| 7,931,649 B2 | | 4/2011 | Couture et al. |
| D649,249 S | | 11/2011 | Guerra |
| D649,643 S | | 11/2011 | Allen, IV et al. |
| D661,394 S | | 6/2012 | Romero et al. |
| 8,333,765 B2 | | 12/2012 | Johnson et al. |
| 8,454,602 B2 | | 6/2013 | Kerr et al. |
| 8,523,898 B2 | | 9/2013 | Bucciaglia et al. |
| 8,529,566 B2 | | 9/2013 | Kappus et al. |
| 8,568,408 B2 | | 10/2013 | Townsend et al. |
| 8,591,510 B2 | | 11/2013 | Allen, IV et al. |
| 8,628,557 B2 | | 1/2014 | Collings et al. |
| 8,679,098 B2 | | 3/2014 | Hart |
| 8,679,140 B2 | | 3/2014 | Butcher |
| 8,685,009 B2 | | 4/2014 | Chernov et al. |
| 8,685,056 B2 | | 4/2014 | Evans et al. |
| 8,696,667 B2 | | 4/2014 | Guerra et al. |
| 8,702,737 B2 | | 4/2014 | Chojin et al. |
| 8,702,749 B2 | | 4/2014 | Twomey |
| 8,745,840 B2 | | 6/2014 | Hempstead et al. |
| 8,747,413 B2 | | 6/2014 | Dycus |
| 8,747,434 B2 | | 6/2014 | Larson et al. |
| 8,752,264 B2 | | 6/2014 | Ackley et al. |
| 8,756,785 B2 | | 6/2014 | Allen, IV et al. |
| 8,845,636 B2 | | 9/2014 | Allen, IV et al. |
| 8,852,185 B2 | | 10/2014 | Twomey |
| 8,864,753 B2 | | 10/2014 | Nau, Jr. et al. |
| 8,864,795 B2 | | 10/2014 | Kerr et al. |
| 8,887,373 B2 | | 11/2014 | Brandt et al. |
| 8,888,771 B2 | | 11/2014 | Twomey |
| 8,900,232 B2 | | 12/2014 | Ourada |
| 8,920,461 B2 | | 12/2014 | Unger et al. |
| 8,939,972 B2 | | 1/2015 | Twomey |
| 8,961,513 B2 | | 2/2015 | Allen, IV et al. |
| 8,961,514 B2 | | 2/2015 | Garrison |
| 8,961,515 B2 | | 2/2015 | Twomey et al. |
| 8,968,283 B2 | | 3/2015 | Kharin |
| 8,968,298 B2 | | 3/2015 | Twomey |
| 8,968,305 B2 | | 3/2015 | Dumbauld et al. |
| 8,968,306 B2 | | 3/2015 | Unger |
| 8,968,307 B2 | | 3/2015 | Evans et al. |
| 8,968,308 B2 | | 3/2015 | Horner et al. |
| 8,968,309 B2 | | 3/2015 | Roy et al. |
| 8,968,310 B2 | | 3/2015 | Twomey et al. |
| 8,968,311 B2 | | 3/2015 | Allen, IV et al. |
| 8,968,317 B2 | | 3/2015 | Evans et al. |
| 8,968,360 B2 | | 3/2015 | Garrison et al. |
| 9,011,435 B2 | | 4/2015 | Brandt et al. |
| 9,023,035 B2 | | 5/2015 | Allen, IV et al. |
| 9,028,492 B2 | | 5/2015 | Kerr et al. |
| 9,033,981 B2 | | 5/2015 | Olson et al. |
| 9,034,009 B2 | | 5/2015 | Twomey et al. |
| 9,039,691 B2 | | 5/2015 | Moua et al. |

(56) References Cited

U.S. PATENT DOCUMENTS

| | | | |
|---|---|---|---|
| 9,039,704 B2 | 5/2015 | Joseph | |
| 9,039,732 B2 | 5/2015 | Sims et al. | |
| 9,060,780 B2 | 6/2015 | Twomey et al. | |
| 9,072,524 B2 | 7/2015 | Heard et al. | |
| 9,113,882 B2 | 8/2015 | Twomey et al. | |
| 9,113,901 B2 | 8/2015 | Allen, IV et al. | |
| 9,113,909 B2 | 8/2015 | Twomey et al. | |
| 9,113,933 B2 | 8/2015 | Chernova et al. | |
| 9,113,934 B2 | 8/2015 | Chernov et al. | |
| 9,113,938 B2 | 8/2015 | Kerr | |
| 9,113,999 B2 | 8/2015 | Taylor et al. | |
| 9,161,807 B2 | 10/2015 | Garrison | |
| 9,192,432 B2 | 11/2015 | Larson et al. | |
| 2003/0114851 A1 | 6/2003 | Truckai et al. | |
| 2004/0153124 A1 | 8/2004 | Whitman | |
| 2005/0033359 A1 | 2/2005 | Dycus | |
| 2006/0224158 A1 | 10/2006 | Odom et al. | |
| 2008/0319442 A1 | 12/2008 | Unger et al. | |
| 2011/0155781 A1 | 6/2011 | Swensgard et al. | |
| 2011/0251612 A1* | 10/2011 | Faller | A61B 18/1445 606/52 |
| 2012/0033030 A1 | 2/2012 | Liu et al. | |
| 2012/0259331 A1 | 10/2012 | Garrison | |
| 2012/0296205 A1 | 11/2012 | Chernov et al. | |
| 2012/0296238 A1 | 11/2012 | Chernov et al. | |
| 2012/0296239 A1 | 11/2012 | Chernov et al. | |
| 2012/0296323 A1 | 11/2012 | Chernov et al. | |
| 2012/0296371 A1 | 11/2012 | Kappus et al. | |
| 2012/0303026 A1 | 11/2012 | Dycus et al. | |
| 2012/0323238 A1 | 12/2012 | Tyrrell et al. | |
| 2013/0018364 A1 | 1/2013 | Chernov et al. | |
| 2013/0022495 A1 | 1/2013 | Allen, IV et al. | |
| 2013/0071282 A1 | 3/2013 | Fry | |
| 2013/0072927 A1 | 3/2013 | Allen, IV et al. | |
| 2013/0079760 A1 | 3/2013 | Twomey et al. | |
| 2013/0079774 A1 | 3/2013 | Whitney et al. | |
| 2013/0085496 A1 | 4/2013 | Unger et al. | |
| 2013/0103030 A1 | 4/2013 | Garrison | |
| 2013/0103031 A1 | 4/2013 | Garrison | |
| 2013/0138101 A1 | 5/2013 | Kerr | |
| 2013/0144284 A1 | 6/2013 | Behnke, II et al. | |
| 2013/0190760 A1* | 7/2013 | Allen, IV | A61B 18/1442 606/52 |
| 2013/0197503 A1 | 8/2013 | Orszulak | |
| 2013/0253489 A1 | 9/2013 | Nau, Jr. et al. | |
| 2013/0255063 A1 | 10/2013 | Hart et al. | |
| 2013/0274736 A1 | 10/2013 | Garrison | |
| 2013/0289561 A1 | 10/2013 | Waaler et al. | |
| 2013/0296922 A1 | 11/2013 | Allen, IV et al. | |
| 2013/0304058 A1 | 11/2013 | Kendrick | |
| 2013/0304066 A1 | 11/2013 | Kerr et al. | |
| 2014/0246473 A1* | 9/2014 | Auld | A61B 17/068 227/175.1 |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 8712328 U1 | 2/1988 |
| DE | 04303882 C2 | 2/1995 |
| DE | 04403252 A1 | 8/1995 |
| DE | 4434938 C1 | 2/1996 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| EP | 1159926 A3 | 3/2003 |
| EP | 1707143 A1 | 10/2006 |
| EP | 1767156 A1 | 3/2007 |
| EP | 2353534 A1 | 8/2011 |
| JP | 61-501068 | 9/1984 |
| JP | 10-24051 A | 1/1989 |
| JP | 11-47150 A | 6/1989 |
| JP | 6502328 | 3/1992 |
| JP | 5-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 3/1996 |
| JP | 08252263 A | 10/1996 |
| JP | 8-289895 A | 11/1996 |
| JP | 8-317934 | 12/1996 |
| JP | 8-317936 A | 12/1996 |
| JP | 9-10223 | 1/1997 |
| JP | 9-122138 A | 5/1997 |
| JP | 0010000195 A | 1/1998 |
| JP | 10-155798 A | 6/1998 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000342599 A | 12/2000 |
| JP | 2000350732 A | 12/2000 |
| JP | 2001008944 A | 1/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-175052 A | 6/2003 |
| JP | 2003245285 A | 9/2003 |
| JP | 2004-517668 A | 6/2004 |
| JP | 2004-528869 A | 9/2004 |
| JP | 2005-253789 A | 9/2005 |
| JP | 2006-015078 A | 1/2006 |
| JP | 2006-501939 A | 1/2006 |
| JP | 2006-095316 A | 4/2006 |
| JP | 2011125195 A | 6/2011 |
| SU | 401367 A1 | 10/1973 |
| WO | 0036986 A1 | 6/2000 |
| WO | 0059392 A1 | 10/2000 |
| WO | 0115614 A1 | 3/2001 |
| WO | 0154604 A1 | 8/2001 |
| WO | 02/45589 A2 | 6/2002 |
| WO | 2004/103156 A2 | 12/2004 |
| WO | 2006021269 A1 | 3/2006 |
| WO | 05110264 A3 | 4/2006 |
| WO | 2007/103986 A2 | 9/2007 |
| WO | 2008040483 A1 | 4/2008 |
| WO | 2008/136837 A1 | 11/2008 |
| WO | 2012/044606 A2 | 4/2012 |

OTHER PUBLICATIONS

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967, British Medical Journal Feb. 6, 1976, vol. 1, nr. 5431 p. 361, ISSN: 0007-1447.

Carbonell et al., "Comparison of theGyrus PlasmaKinetic Sealer and the Valleytab LigaSure Device in the Hemostasis of Small,

(56) References Cited

OTHER PUBLICATIONS

Medium and Large-Sized Arteries" Carolinas Laparoscopic and Advanced Surgery Program, Carolinas Laparoscopic and AdvancedSurgery Program, Carolinas Medical Center, Charlotte, NC.
Peterson et al. "Comparison of Healing Process Following Ligation with Sutures and Bipolar Vessel Sealing" Surgical Technology International (2001).
"Electrosurgery: A Historical Overview" Innovations in Electrosurgery; Sales/Product Literature; Dec. 31, 2000.
Johnson et al. "Evaluation of a Bipolar Electrothermal Vessel Sealing Device in Hemorrhoidectomy" Sales/Product Literature; Jan. 2004.
E. David Crawford "Evaluation of a New Vessel Sealing Device in Urologic Cancer Surgery" Sales/Product Literature 2000.
Johnson et al. "Evaluation of the LigaSure Vessel Sealing System in Hemorrhoidectormy" American College of Surgeons (ACS) Clinicla Congress Poster (2000).
Muller et al., "Extended Left Hemicoletomy Using the LigaSure Vessel Sealing System" Innovations That Work,. quadrature.Sep. 1999.
Kennedy et al. "High-burst-strength, feedback-controlled bipolar vessel sealing" Surgical Endoscopy (1998) 12: 876-878.
Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.
Carus et al., "Initial Experience With the LigaSure Vessel Sealing System in Abdominal Surgery" Innovations That Work,.quadrature. Jun. 2002.
Heniford et al. "Initial Research and Clinical Results with an Electrothermal Bipolar Vessel Sealer" Oct. 1999.
Heniford et al. "Initial Results with an Electrothermal Bipolar Vessel Sealer" Surgical Endoscopy (2000) 15:799-801.
Herman et al., "Laparoscopic Intestinal Resection With the LigaSure Vessel Sealing System: A Case Report"; Innovations That Work, Feb. 2002.
Koyle et al., "Laparoscopic Palomo Varicocele Ligation in Children and Adolescents" Pediatric Endosurgery & Innovative Techniques, vol. 6, No. 1, 2002.
W. Scott Helton, "LigaSure Vessel Sealing System: Revolutionary Hemostasis Product for General Surgery"; Sales/Product Literature 1999.
LigaSure Vessel Sealing System, the Seal of Confidence in General, Gynecologic, Urologic, and Laparaoscopic Surgery; Sales/Product Literature; Apr. 2002.
Joseph Ortenberg "LigaSure System Used in Laparoscopic 1st and 2nd Stage Orchiopexy" Innovations That Work, Nov. 2002.
Sigel et al. "The Mechanism of Blood Vessel Closure by High Frequency Electrocoagulation" Surgery Gynecology & Obstetrics, Oct. 1965 pp. 823-831.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Paul G. Horgan, "A Novel Technique for Parenchymal Division During Hepatectomy" The American Journal of Surgery, vol. 181, No. 3, Apr. 2001 pp. 236-237.
Benaron et al., "Optical Time-Of-Flight and Absorbance Imaging of Biologic Media", Science, American Association for the Advancement of Science, Washington, DC, vol. 259, Mar. 5, 1993, pp. 1463-1466.
Olsson et al. "Radical Cystectomy in Females" Current Surgical Techniques in Urology, vol. 14, Issue 3, 2001.
Palazzo et al. "Randomized clinical trial of Ligasure versus open haemorrhoidectomy" British Journal of Surgery 2002, 89, 154-157.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
"Reducing Needlestick Injuries in the Operating Room" Sales/Product Literature 2001.
Bergdahl et al. "Studies on Coagulation and the Development of an Automatic Computerized Bipolar Coagulator" J. Neurosurg, vol. 75, Jul. 1991, pp. 148-151.
Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.
Seyfan et al. "Sutureless Closed Hemorrhoidectomy: A New Technique" Annals of Surgery vol. 234 No. 1, Jul. 2001 pp. 21-24.
Levy et al., "Update on Hysterectomy—New Technologies and Techniques" OBG Management, Feb. 2003.
Dulemba et al. "Use of a Bipolar Electrothermal Vessel Sealer in Laparoscopically Assisted Vaginal Hysterectomy" Sales/Product Literature; Jan. 2004.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Sengupta et al., "Use of a Computer-Controlled Bipolar Diathermy System in Radical Prostatectomies and Other Open Urological Surgery" ANZ Journal of Surgery (2001) 71.9 pp. 538-540.
Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.
E. David Crawford "Use of a Novel Vessel Sealing Technology in Management of the Dorsal Veinous Complex" Sales/Product Literature 2000.
Jarrell et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632, Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869, filed Sep. 10, 1997, James G. Chandler.
U.S. Appl. No. 09/177,950, filed Oct. 23, 1998, Randel A. Frazier.
U.S. Appl. No. 09/387,883, filed Sep. 1, 1999, Dale R Schmaltz.
U.S. Appl. No. 09/591,328, filed Jun. 9, 2000, Thomas P. Ryan.
U.S. Appl. No. 12/336,970, filed Dec. 17, 2008, Paul R. Sremeich.
U.S. Appl. No. 13/050,182, filed Mar. 17, 2011, Glenn A. Horner.
U.S. Appl. No. 13/085,144, filed Apr. 12, 2011, Keir Hart.
European Search Report from corresponding application EP 12196678 dated May 10, 2013.
Extended European Search Report for application No. 15 19 1593 dated Jun. 15, 2016.

\* cited by examiner

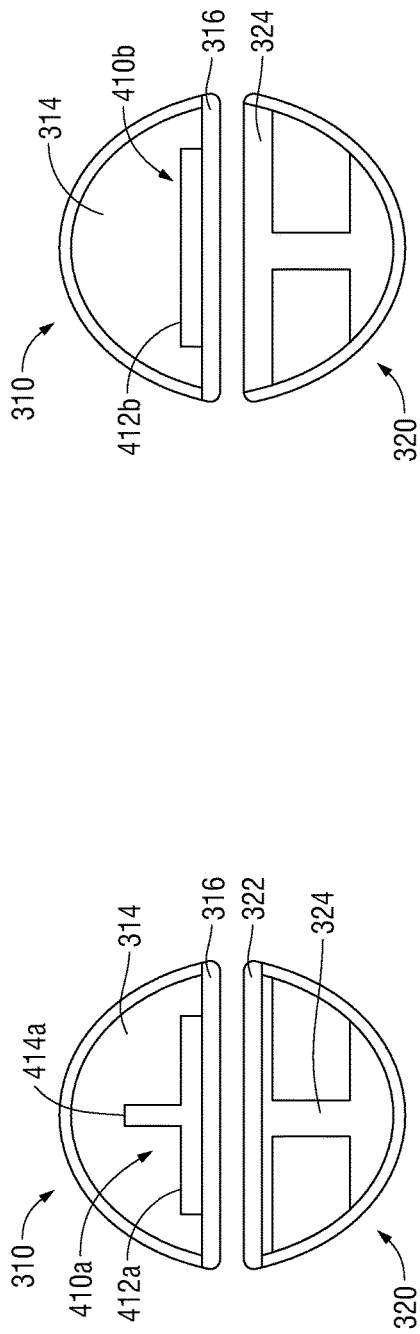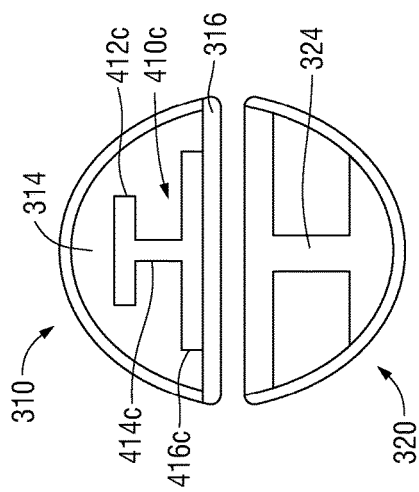

SURGICAL INSTRUMENTS WITH FORCE APPLIER AND METHODS OF USE

CROSS REFERENCE TO RELATED APPLICATION

The present application claims the benefit of and priority to U.S. Provisional Application Ser. No. 62/105,961, filed on Jan. 21, 2015, the entire contents of which are incorporated herein by reference.

BACKGROUND

Technical Field

The present disclosure relates to surgical instruments and, more particularly, to surgical instruments including a force applier for grasping, treating, sealing, stapling, and/or dividing tissue.

Description of Related Art

Many surgical instruments are known for sealing, stapling, or otherwise joining tissue. Some of these surgical include one or more movable handles, levers, actuators, triggers, etc. for actuating and/or manipulating one or more functional components of the surgical instrument. For example, a surgical forceps may include a movable handle that is selectively actuatable relative to a stationary handle for moving at least one jaw member with respect to another jaw member of the forceps between spaced-apart and approximated positions for grasping tissue therebetween. Such a forceps may further include additional triggers for selectively actuating electrosurgical energy or for deploying staples, and/or for deploying a knife between the jaw members to cut tissue grasped therebetween.

In certain types of surgical procedures, e.g., lobectomies, segmentectomies, nephrectomies, etc., when a surgeon wishes to seal thick tissue, such as lung parenchyma tissue or solid organ tissue, traditional sealing methods may not be desired due to the thickness and strength of the target tissue. Accordingly, a surgical instrument for joining thick tissue may be useful.

SUMMARY

The present disclosure relates to a surgical instrument including a housing, an elongated portion, an end effector, a drive beam and a force applier. The housing includes a first actuator and a second actuator. The elongated portion extends distally from the housing and defines a longitudinal axis. The end effector is disposed adjacent a distal portion of the elongated portion, and includes a first jaw member and a second jaw member. The first jaw member has a cavity defined therein. The first jaw member is movable relative to the second jaw member between an open position and an approximated position. The first jaw member applies a first force against tissue disposed between the jaw members. At least a partial actuation of the first actuator causes distal translation of the drive beam to move the first jaw member relative to the second jaw member toward the approximated position. At least a partial actuation of the second actuator causes distal translation of the force applier such that at least a portion of the force applier moves into the cavity of the first jaw member and applies an additional force against tissue disposed between the jaw members.

In disclosed embodiments, at least a partial actuation of the second actuator in a first direction causes distal translation of the force applier, and that at least a partial actuation of the second actuator in a second direction causes proximal translation of the force applier. It is additionally disclosed that the force applier is translatable only when the jaw members are disposed in the approximated position.

In disclosed embodiments, the surgical instrument further includes a third actuator and a knife assembly. The third actuator is disposed in mechanical cooperation with the housing, and the knife assembly is in mechanical cooperation with the third actuator. The third actuator is selectively and independently actuatable with respect to the first actuator and the second actuator. At least a partial actuation of the third actuator causes distal translation of the knife assembly.

It is further disclosed that at least one of the jaw members includes a sensor configured to determine thickness of tissue held between the jaw members, and/or a sensor configured to detect a pulse within tissue held between the jaw members.

The present disclosure also relates to a method of treating tissue. The method comprises clamping tissue between two jaw members of a surgical instrument, advancing, after the tissue is clamped, a force applier through a cavity of one of the jaw members of the surgical instrument, and activating electrosurgical energy through the tissue.

In disclosed embodiments, the method further comprises retracting the force applier such that the force applier is free from contact with the jaw members. It is also disclosed that retracting the force applier is performed while the tissue is clamped between the jaw members. It is additionally disclosed that the tissue remains clamped between the jaw members while the force applier is retracted and free from contact with the jaw members. Further, it is disclosed that the method further comprises advancing the force applier a second time through the cavity of one of the jaw members of the surgical instrument. Additionally, it is disclosed that activating electrosurgical energy through the tissue is performed after advancing the force applier at least a second time.

In disclosed embodiments, the method further comprises perfusing blood from the tissue held between the jaw members by retracting the force applier from the cavity of the jaw member, and advancing and retracting the force applier a subsequent number of times through the cavity of the jaw member. It is further disclosed that the method includes detecting a pulse from the tissue held between the jaw members using at least one sensor disposed on the first jaw member. It is additionally disclosed to seal the tissue held between the jaw members after the pulse is within a predetermined range. In disclosed embodiments, the method includes determining thickness of the tissue held between the jaw members using at least one sensor disposed on the first jaw member. It is further disclosed that the method includes sealing the tissue held between the jaw members after the thickness of the tissue is within a predetermined range.

BRIEF DESCRIPTION OF THE DRAWINGS

Various aspects of the present disclosure are described herein with reference to the drawings wherein like reference numerals identify similar or identical elements:

FIG. 6A is a transverse cross-sectional view taken along line 6A of FIG. 5 illustrating one embodiment of the jaw members;

FIGS. 6B and 6C are transverse cross-sectional views of alternate embodiments of the jaw members of FIG. 6A.

DETAILED DESCRIPTION

Figure 1:
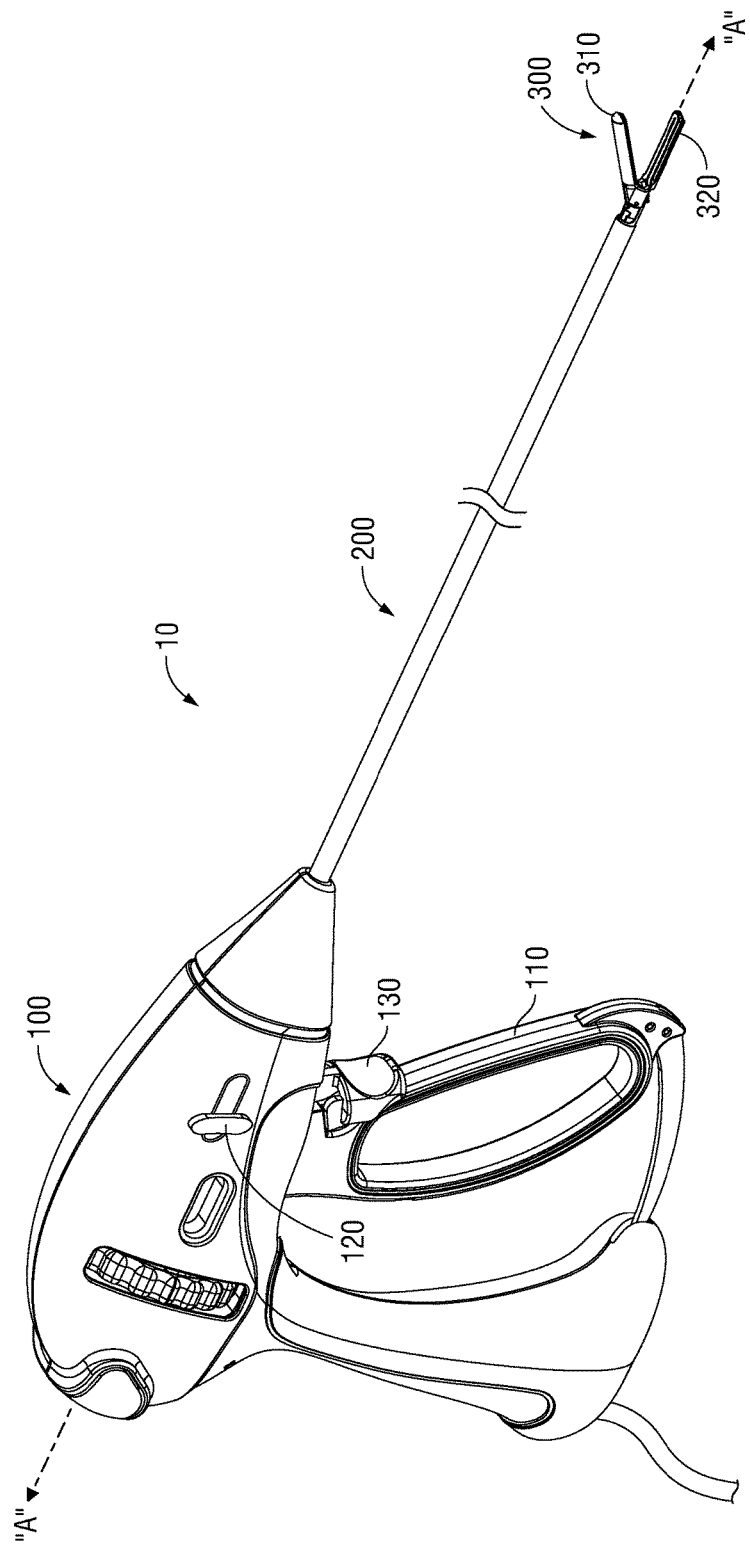
FIG. 1 is a perspective view of an embodiment of a surgical instrument in accordance with the present disclosure.

Embodiments of the presently disclosed surgical instrument are described in detail with reference to the drawings, in which like reference numerals designate identical or corresponding elements in each of the several views. As used herein the term "distal" refers to that portion of the surgical instrument that is farther from the user, while the term "proximal" refers to that portion of the surgical instrument that is closer to the user.

Referring initially to FIG. 1, an embodiment of a surgical instrument 10 is shown for use with various surgical procedures and generally includes a housing 100, an elongated (e.g., endoscopic) portion 200 extending distally from housing 100 and defining a first longitudinal axis "A-A," and an end effector 300 disposed adjacent a distal portion of elongated portion 200. Housing 100 includes a first actuator or handle 110, a second actuator 120 and a third actuator 130 operably associated therewith. End effector 300 includes a first jaw member 310 and a second jaw member 320. Surgical instrument 10 may be configured to connect to a source of electrosurgical energy (not shown) or contain an independent energy source e.g., a battery (not shown).

Figure 2:
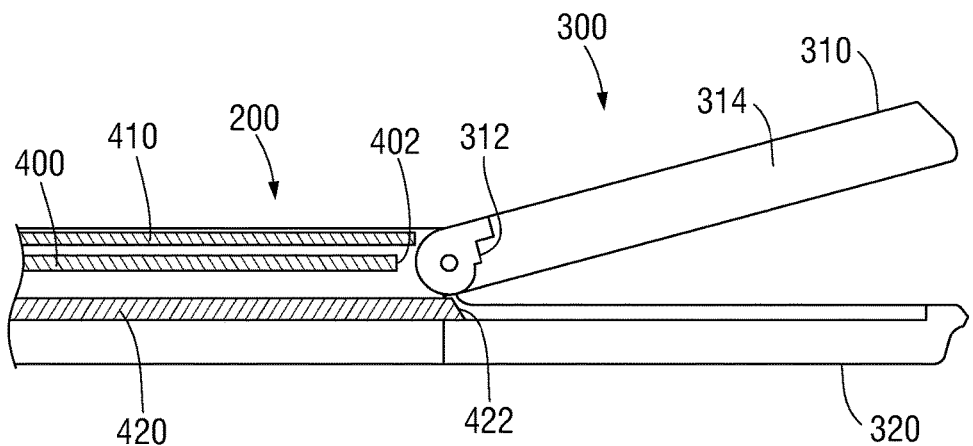
FIG. 2 is a cross-sectional view of a distal end of the surgical instrument of FIG. 1, illustrating jaw members in an open position, a drive beam in a proximal position, a force applier in a proximal position, and a knife assembly in a proximal position.
Figure 3:
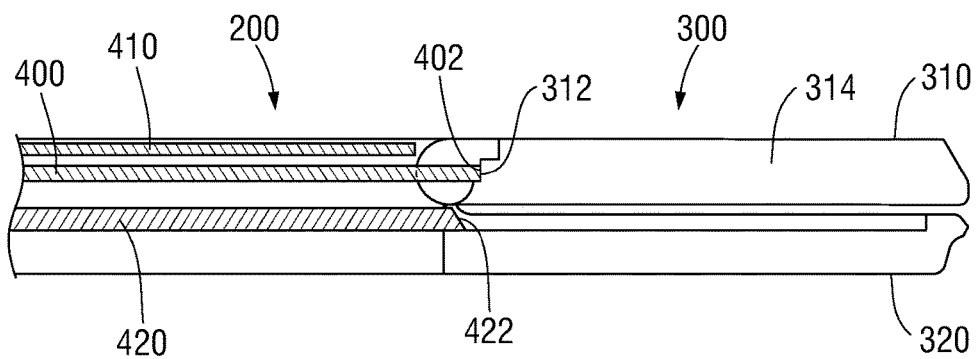
FIG. 3 is a cross-sectional view of the distal end of the surgical instrument of FIG. 1, illustrating the jaw members in an approximated position, the drive beam in a distal position, the force applier in a proximal position, and the knife assembly in a proximal position.
Figure 4:
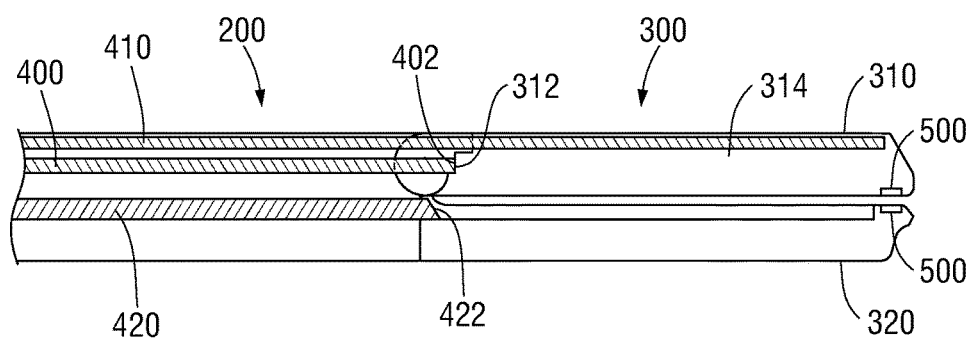
FIG. 4 is a cross-sectional view of the distal end of the surgical instrument of FIG. 1, illustrating the jaw members in an approximated position, the drive beam in a distal position, the force applier in a distal position, and the knife assembly in a proximal position.
Figure 5:
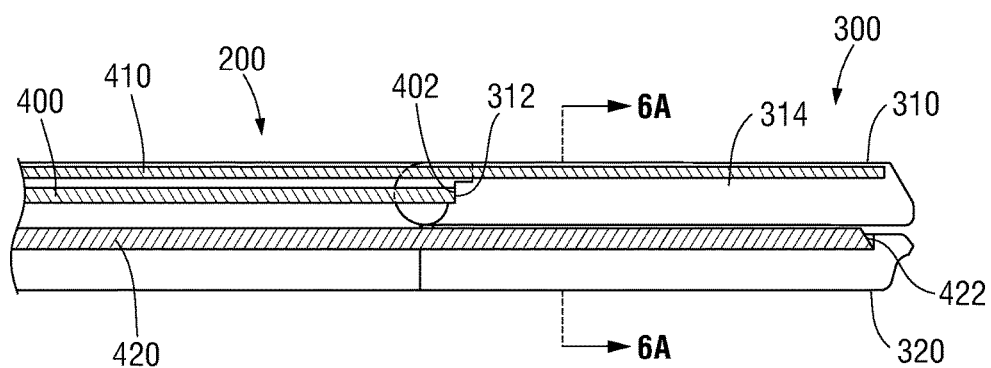
FIG. 5 is a cross-sectional view of the distal end of the surgical instrument of FIG. 1, illustrating the jaw members in an approximated position, the drive beam in a distal position, the force applier in a distal position, and the knife assembly in a distal position.

With reference to FIGS. 2-5, various stages of operation of surgical instrument 10 are shown. First jaw member 310 is pivotably engaged with second jaw member 320 and is movable between a first, open position (FIGS. 1 and 2) and a second, approximated position (FIGS. 3-5). In the illustrated embodiments, second jaw member 320 is fixed from pivotable movement with respect to elongated portion 200 of surgical instrument 10 (unilateral jaw movement).

With particular reference to FIG. 2, first jaw member 310 and second jaw member 320 are shown in the open position, a drive beam 400 is shown in a proximal position, a force applier 410 is shown in a proximal position, and a knife assembly 420 is shown in a proximal position. Each actuator 110, 120, 130 is configured to independently actuate one of drive beam 400, force applier 410, and knife assembly 420, respectively. While it is described herein that first actuator or handle 110 is mechanically engaged with drive beam 400, second actuator 120 is mechanically engaged with force applier 410, and third actuator 130 is mechanically engaged with knife assembly 420, any variation of such is within the scope of the present disclosure.

Drive beam 400 is mechanically engaged with first actuator or handle 110 of housing 100, such that at least a partial actuation of first actuator or handle 110 causes longitudinal translation drive beam 400 in a first (e.g., distal) direction. With reference to FIGS. 2-3, a predetermined amount of actuation of first actuator or handle 110 causes a distal end 402 of drive beam 400 to move from a first position where distal end 402 is spaced from a camming surface 312 of first jaw member 310 (FIG. 2), into a second position where distal end 402 is in contact with camming surface 312 (FIG. 3). The engagement between distal end 402 of drive beam 400 and camming surface 312 of first jaw member 310 causes jaw member 310 to pivot with respect to second jaw member 320 and move toward its approximated position (FIG. 3). Additionally, moving first actuator or handle 110 toward its initial, pre-actuated position causes longitudinal translation drive beam 400 in a second (e.g., proximal) direction, which causes first jaw member 310 to move back towards its open position (FIG. 2). The first jaw member 310 may be biased toward its open position.

Various handle assemblies for actuating first actuator or handle 110 and corresponding drive assemblies (not shown) are contemplated for translating drive beam 400 and are discussed in commonly-owned U.S. Pat. No. 7,857,812, the entire contents of which are incorporated by reference herein.

Next, prior to applying energy from at least one jaw member 310, 320 through tissue held therebetween (as is typically done after approximation of jaw members 310, 320), a user can selectively and independently actuate second actuator 120, which is mechanically engaged with force applier 410, in a first direction. Force applier 410 is configured for longitudinal translation in response to at least a partial actuation of second actuator 120. Distal translation of force applier 410 causes at least a portion of the force applier 410 to travel at least partially through a cavity 314 within first jaw member 310 (see FIG. 4). The distal translation of force applier 410 at least partially through cavity 314 exerts an additional force (in addition to the force applied by approximation of first jaw member 310) upon tissue held between first jaw member 310 and second jaw member 320.

It is contemplated that actuation of the first actuator or handle 110 applies a force to the jaw members 310 and 320 in the range of about 3 kg/cm$^2$ to about 16 kg/cm$^2$, and that actuation of the second actuator 120 applies an additional force to the jaw members 310 and 320 and into tissue. It is contemplated that the force applied by force applier 410 in response to actuation of the second actuator 120 is dependent on several variables, such as the thickness of the tissue to be clamped, the type of the tissue to be clamped, the area of the tissue contacting surfaces of the jaw members 310 and 320, etc.

Also, in the closed or approximated configuration, a separation or gap distance may be maintained between the jaw members 310 and 320 by an array of stop members (not shown). In some embodiments, to provide an effective tissue seal, an appropriate gap distance of between about 0.001 inches to about 0.006 inches may be provided.

The advancement of force applier 410 perfuses or displaces blood from the tissue held between jaw members 310, 320. A user may wish to consecutively and/or rapidly (e.g., once every one to five seconds, for instance) at least partially advance and at least partially retract force applier 410 to obtain the desired perfusion effect.

A user may desire such an additional force when performing a surgical procedure on thick tissue, e.g., when performing lobectomies or segmentectomies on lung parenchyma. If a user, e.g., clinician, decides that additional force is desired (e.g., if the tissue between jaw members 310 and 32, such as tissue between distal portions of the jaw members 310 and 320, is still too thick), the user may move second actuator 120 in a second direction to retract force applier 410 (i.e., move force applier 410 in a proximal direction). As can be appreciated, since first actuator or handle 110 and second actuator 120 are selectively and independently actuatable, drive beam 400 can remain in an advanced position, which corresponds to jaw members 310, 320 remaining approximated (while grasping tissue therebetween), when force applier 410 is retracted (FIG. 3). The user may then move second actuator 120 in the first direction to distally advance force applier 410 to apply an additional force to the tissue held between jaw members 310, 320. The advancement and retraction of force applier 410 can be performed any number of times while jaw members 310, 320 are approximated.

Once the user determines the tissue is sufficiently clamped and/or perfused, the user may desire to join (e.g., seal, staple or treat) the tissue. In instances where surgical instrument 10 is an electrosurgical instrument, the user may activate electrosurgical energy such that energy flows from the first jaw member 310 to the second jaw member 320, to effect a tissue seal. In instances where surgical instrument 10 is a surgical stapling instrument, the user may advance a drive member to force fasteners from one jaw member, e.g., first jaw member 310, toward the other jaw member, e.g., second jaw member 320. Further details of an electrosurgical instrument are disclosed in U.S. Pat. Nos. 7,101,371 and 7,083,618, the entire contents of which being incorporated by reference herein. Further details of a surgical stapling instrument are disclosed in U.S. Pat. No. 6,953,139, the entire contents of which being incorporated by reference herein.

To help a user determine whether the tissue between jaw members 310, 320 is sufficiently clamped, surgical instrument 10 may include one or more sensors 500. In the embodiment illustrated in FIG. 4, each jaw member 310, 320 includes a sensor 500. In disclosed embodiments, sensors 500 (or at least one of the sensors 500) are proximity sensors, which can detect how close the sensors 500 are to each other. Sensors 500 are in electrical communication (e.g., wired or wireless) with a receiver (e.g., on housing 100 or located remotely), and the receiver may provide a visual, audile and/or tactile indication to notify the user that the information measured or detected by sensors 500 is within a desired range, thus indicating the thickness of the clamped tissue is in a desired range. One sensor 500 (or both sensors) may be configured to detect the amount of blood in the clamped tissue (e.g., by detecting the pulse). Here, too, the receiver can notify the user that the amount of blood in the clamped tissue is within a desired range.

The use of sensor(s) 500 may be part of a robotic system, discussed below, which can automatically retract and advance force applier 410 an appropriate number of times and for an appropriate duration based on information received from sensor(s) 500 as compared to predetermined values of desired tissue thickness and/or amount of blood.

Next, and with particular reference to FIG. 5, a user may at least partially actuate third actuator 130 to distally advance knife assembly 420 to sever tissue. More particularly, distal advancement of knife assembly 420 causes a knife blade 422 of knife assembly 420 to be advanced through tissue held between jaw members 310, 320, thus severing the tissue. Surgical instrument 10 may include features that physically prevent the knife assembly 420 from advancing when the jaw members 310, 320 are in their first, open position (FIG. 2).

With reference to FIGS. 6A-6C, various embodiments of jaw members 310 and 320 are shown. FIG. 6A illustrates first jaw member 310 including cavity 314, a seal plate 316, and a first embodiment of force applier 410a within cavity 314. Here, force applier 410a includes a "T" cross-section having a horizontal beam 412a and a vertical beam 414a. Second jaw member 320 includes a seal plate 322 for bipolar sealing, and an I-beam 324, e.g., for providing additional strength to the second jaw member 320.

FIG. 6B illustrates first jaw member 310 including cavity 314, seal plate 316, and a second embodiment of force applier 410b within cavity 314. Here, force applier 410b includes a linear cross-section having a horizontal beam 412b. Second jaw member 320 lacks a seal plate, and includes I-beam 324, e.g., for additional strength. Thus, surgical instrument 10 is configured for monopolar sealing.

FIG. 6C illustrates first jaw member 310 including cavity 314, seal plate 316, and a third embodiment of force applier 410c within cavity 314. Here, force applier 410c includes an "I"-shaped cross-section having a first horizontal beam 412c, a vertical beam 414c, and a second horizontal beam 416c. Second jaw member 320 lacks a seal plate, and includes I-beam 324, e.g., for additional strength. Thus, surgical instrument 10 is configured for monopolar sealing.

The present disclosure also includes combinations of the embodiments of FIGS. 6A-6C and variations of those embodiments, including variations in width, height, length, thickness and/or shape of the various components described and illustrated herein. Additionally, force applier 410 may be made of any suitable material, e.g., steel, for providing the desired strength.

Moreover, the end effector assembly 300 may include a bilateral jaw member arrangement wherein both jaw members 310, 320 are moveable by first actuator or handle 110. Second actuator 120 may be configured to translate the force applier 410 into one or both jaw members 310 and 320 to provide an additional clamping force on tissue disposed between jaw members 310 and 320.

The present disclosure also relates to methods of joining (e.g., sealing, fastening, etc.) tissue. The methods include using surgical instrument 10, as described above, to join thick tissue, to join thick and wide tissue, to join lung parenchyma, to perform a lobectomy, and to perform a segmentectomy, for example. Methods also include advancing drive beam 400 to approximate at least one jaw member (e.g., 310) with respect to the other jaw member (e.g., 320), advancing force applier 410 such that force applier 410 extends at least partially through cavity 314 of one or both jaw members (e.g., jaw member 310), retracting force applier 410 from engagement with cavity 314 while drive beam 400 remains in an advanced position, advancing force applier 410 a second time such that force applier 410 extends at least partially through cavity 314 of one or both jaw members (e.g., jaw member 310), and joining tissue held between jaw members 310, 320.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 7:
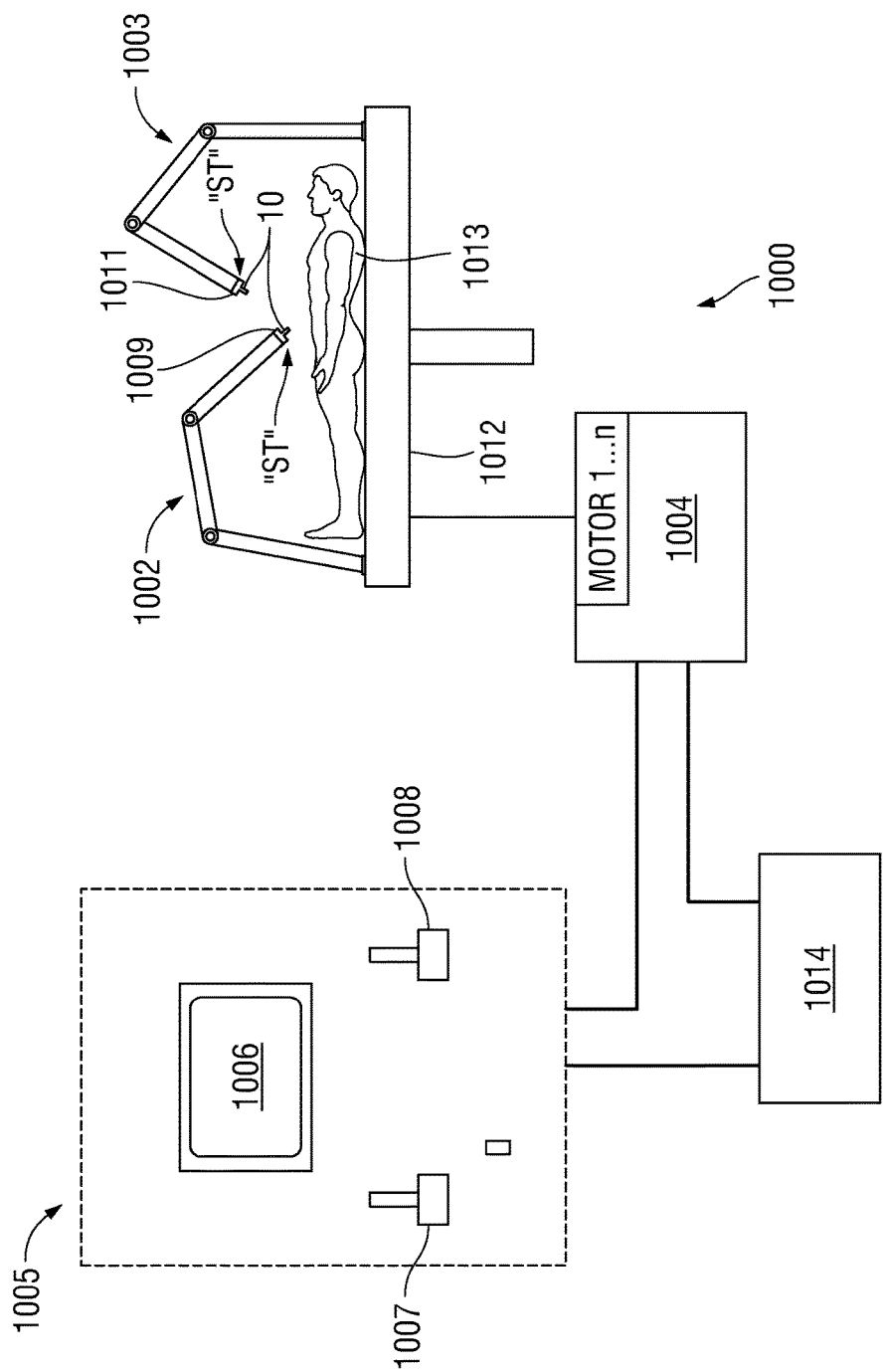
FIG. 7 is a schematic illustration of a surgical system in accordance with the present disclosure.

With particular reference to FIG. 7, a medical work station is shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus surgical instrument 10 (including end effector 300) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A surgical instrument, comprising:
a housing including a first actuator and a second actuator;
an elongated portion extending distally from the housing and defining a longitudinal axis;
an end effector disposed adjacent a distal portion of the elongated portion, the end effector including a first jaw member and a second jaw member, the first jaw member having a cavity defined therein, the first jaw member movable relative to the second jaw member between an open position and an approximated position, wherein the first jaw member applies a first force against tissue disposed between the jaw members;
a drive beam disposed in mechanical cooperation with the first actuator, the first actuator selectively and independently actuatable with respect to the second actuator, wherein at least a partial actuation of the first actuator causes distal translation of the drive beam to move the first jaw member relative to the second jaw member toward the approximated position; and
a force applier disposed in mechanical cooperation with the second actuator, the second actuator selectively and independently actuatable with respect to the first actuator, wherein at least a partial actuation of the second actuator causes distal translation of the force applier such that at least a portion of the force applier moves into the cavity of the first jaw member and applies an additional force against tissue disposed between the jaw members, and wherein a distal-most end of the force applier is entirely within a distal end of the first jaw member when the force applier is in a distal-most position.

2. The surgical instrument according to claim 1, wherein at least a partial actuation of the second actuator in a first direction causes distal translation of the force applier, and wherein at least a partial actuation of the second actuator in a second direction causes proximal translation of the force applier.

3. The surgical instrument according to claim 2, wherein the force applier is translatable only when the jaw members are disposed in the approximated position.

4. The surgical instrument according to claim 1, further comprising a third actuator and a knife assembly, wherein the third actuator is disposed in mechanical cooperation with the housing, and wherein the knife assembly is in mechanical cooperation with the third actuator, the third actuator selectively and independently actuatable with respect to the first actuator and the second actuator, wherein at least a partial actuation of the third actuator causes distal translation of the knife assembly.

5. The surgical instrument according to claim 1, wherein at least one of the jaw members includes a sensor configured to determine thickness of tissue held between the jaw members.

6. The surgical instrument according to claim 1, wherein at least one of the jaw members includes a sensor configured to detect a pulse within tissue held between the jaw members.

\* \* \* \* \*